United States Patent [19]

Adams et al.

[11] Patent Number: 5,223,712

[45] Date of Patent: Jun. 29, 1993

[54] CLOSED LOOP IONIZATION APPARATUS FOR DETECTING TRACE GASES

[75] Inventors: Horst Adams, Nonnenhorn; Joerg Boscher, Kiel; Dirk Hoffmeyer, Altenholz, all of Fed. Rep. of Germany

[73] Assignee: Honeywell-Elac-Nautik GmbH, Kiel, Fed. Rep. of Germany

[21] Appl. No.: 730,957

[22] PCT Filed: Feb. 7, 1990

[86] PCT No.: PCT/EP90/00195

§ 371 Date: Jul. 19, 1991

§ 102(e) Date: Jul. 19, 1991

[87] PCT Pub. No.: WO90/09586

PCT Pub. Date: Aug. 23, 1990

[30] Foreign Application Priority Data

Feb. 11, 1989 [DE] Fed. Rep. of Germany ....... 3904168

[51] Int. Cl.⁵ ............................................. G01N 27/62
[52] U.S. Cl. .................................... 250/281; 250/288; 250/384
[58] Field of Search ........... 250/281, 282, 283, 288 R, 250/287, 382, 384; 324/464; 422/83, 93, 98

[56] References Cited

U.S. PATENT DOCUMENTS

| | | | |
|---|---|---|---|
| 3,558,283 | 1/1971 | Freeman | 436/143 |
| 3,569,825 | 3/1971 | Lillenfeld | 324/464 |
| 3,596,088 | 12/1969 | Cohen | 250/287 |
| 4,445,038 | 4/1984 | Spangler | 250/287 |
| 4,551,624 | 11/1985 | Spangler | 250/287 |

*Primary Examiner*—Jack I. Berman
*Assistant Examiner*—James Beyer
*Attorney, Agent, or Firm*—Charles L. Rubow

[57] ABSTRACT

A trace gas detector including in a closed gas loop, two baffle cells with an intermediate trace gas filter, each baffle cell consists of an ionization source, a labyrinth-like recombination zone and a collector electrode. A differential circuit derives a differential signal from output signals of the two baffle cells, the differential signal depending only on the trace gas concentration. Temperature changes and supply voltage changes are compensated by means of the differential circuit.

7 Claims, 2 Drawing Sheets

CLOSED LOOP IONIZATION APPARATUS FOR DETECTING TRACE GASES

BACKGROUND OF THE INVENTION

The invention relates to detection of small concentrations of trace gases in a carrier gas, and, in particular, to apparatus for detecting the loading of air with war gases.

U.S. Pat. No. 3,558,283 describes a method of determining the reactive hydrocarbon content of automotive or exhaust gases, whereat a stream of said gases is brought into contact with electrically heated combustion filaments in opposed arms of a Wheatstone bridge. Afterwards the reactive hydrocarbons are removed from the stream by passing that stream through a stripping column and then passing this stream over the opposed other arms of the same bridge and applying the output of the Wheatstone bridge to provide a signal corresponding to the amount of reactive hydrocarbons in the exhaust gases. In a second embodiment shown in the same U.S. patent the gas stream is split into two equal portions, whereat one of them is subject to combustion. The reactive hydrocarbons are removed from the other of said portions by passing it through a stripping column and afterwards subjecting said other portion also to combustion. Finally the heat effects of combustion of the two portions are converted into electrical signals and by means of a differential amplifier are converted to an electrical signal corresponding to the amount of reactive hydrocarbons in the exhaust gases.

The first method comprising the Wheatstone bridge arrangement requires four separate measuring chambers and therewith is complicated. The second version strongly depends on both portions of the gas stream being maintained equal. The same applies to other measuring apparatus using two parallel gas streams, such as the apparatuses described in U.S. Pat. Nos. 3,997,297 and 3,620,931.

U.S. Pat. No. 3,835,328 describes a baffle cell measuring apparatus for detecting small concentrations of trace gases, where a gas mixture containing said trace gases flows through a cell containing a radiation source for ionizing the gas molecules, a recombination zone consisting of baffles or which provide a labyrinth-like flow path of increased length and a collector electrode at the outlet of said recombination zone. Further improvements of this ionization detector are described in U.S. Pat. Nos. 4,075,550, 4,238,678 and 4,362,941. In all those known baffle cells an airstream is generated through the cell by means of a ventilator or a pump. At the input of the cell an ionization means such as a radiation source is provided and the gas stream flows through a flow path, the length of which is increased in the form of a labyrinth. Within this labyrinth path most of the ionized carrier gas molecules recombine, whereat the trace gases together with ions of the carrier gas form molecule packets or clusters which do not recombine within said labyrinth. These clusters rather move to the collector electrode and there generate a corresponding electrical current.

Problems arise if the trace gas such as mustard gas is present only in very small concentrations and therefor the generated electrical currents are only available in the range of $10^{-12}A$ ($10^{-12}A = 1pA$). In those cases the measuring signal might be covered by the noise of the subsequent amplifier. Furthermore, one cannot be sure that all ionized carrier gas molecules really recombine so that by non-recombined carrier gas molecules a further interference signal may be generated. Particular difficulties arise if the detector has to be used in a large temperature range such as from $-30°$ C. to $+50°$ C. and is expected to measure accurately over the entire range. Furthermore, it is desired that changes of the supply voltage or any external electromagnetic radiation should not influence the measuring result.

SUMMARY OF THE INVENTION

It is the object of the invention to produce a trace gas detector, in particular a mustard gas detector, sometimes called LOST detector, whose accuracy and reliability is not impaired by internal interference such as non-recombined carrier gas ions or a remainder of water vapor, or by external interferences such as temperature changes, changes of the supply voltages or external electromagnetic radiation. These and other objects are achieved by a detecting apparatus, whereat a first baffle cell together with a filter for the trace gases to be detected, a gas flow generating means, and with a second baffle cell provided downstream of said filter forms a closed gas loop, so that there is the same flow through both cells. The source and collector electrodes of the two cells are interconnected to produce an output signal corresponding to the concentration of the trace gas to be detected. The baffle cell located in the closed gas loop in front of the filter and/or in front of the drying means delivers an output current which depends on the trace gas to be detected as well as on eventual internal interference influences. However, the baffle cell detector behind the filter and/or the drying means responds only to those interference influences. Forming the difference of the two output signals removes the influence of those internal and external interferences so that the differential output signal depends only on the concentration of the trace gas.

A further problem arises during the detection of blister agents, in particular sulfur-LOST (mustard gas $S(CH_2CH_2)_2CL_2$) and nitrogen-LOST ($N(CH_2CH_2Cl)_3$) insofar as a high concentration of water vapor impedes the formation of trace gas clusters. This problem can be solved in that according to a further improvement of the invention the gas mixture is fed to the closed gas loop via a water vapor barrier such as a silicon diaphragm. This closed gas loop then only contains a very small remainder of water vapor which in addition by means of a dryer can be stabilized to a dew point lower than $-30°$ C. Such dryer simultaneously works as a filter or can be combined with an active charcoal filter. The invention discloses a compact trace gas detector which doesn't need high voltage but can be operated from low voltage batteries. The detector does not require gas flow control means for maintaining identical flow in two parallel branches because both cells are connected in series and the same stream flows through them. Said detector in view of its small power consumption and small dimensions can be combined with another detector responsive to other war gases, such as nerve agents, into a compact universal detector. A suitable nerve agent detector comprising a so-called dynamic grid cell is described in U.S. Pat. No. 4,775,795.

BRIEF DESCRIPTION OF THE DRAWINGS

The invention will now be described with reference to a preferred embodiment shown in the drawing. In this drawing

DESCRIPTION OF THE PREFERRED EMBODIMENT

Figure 1:
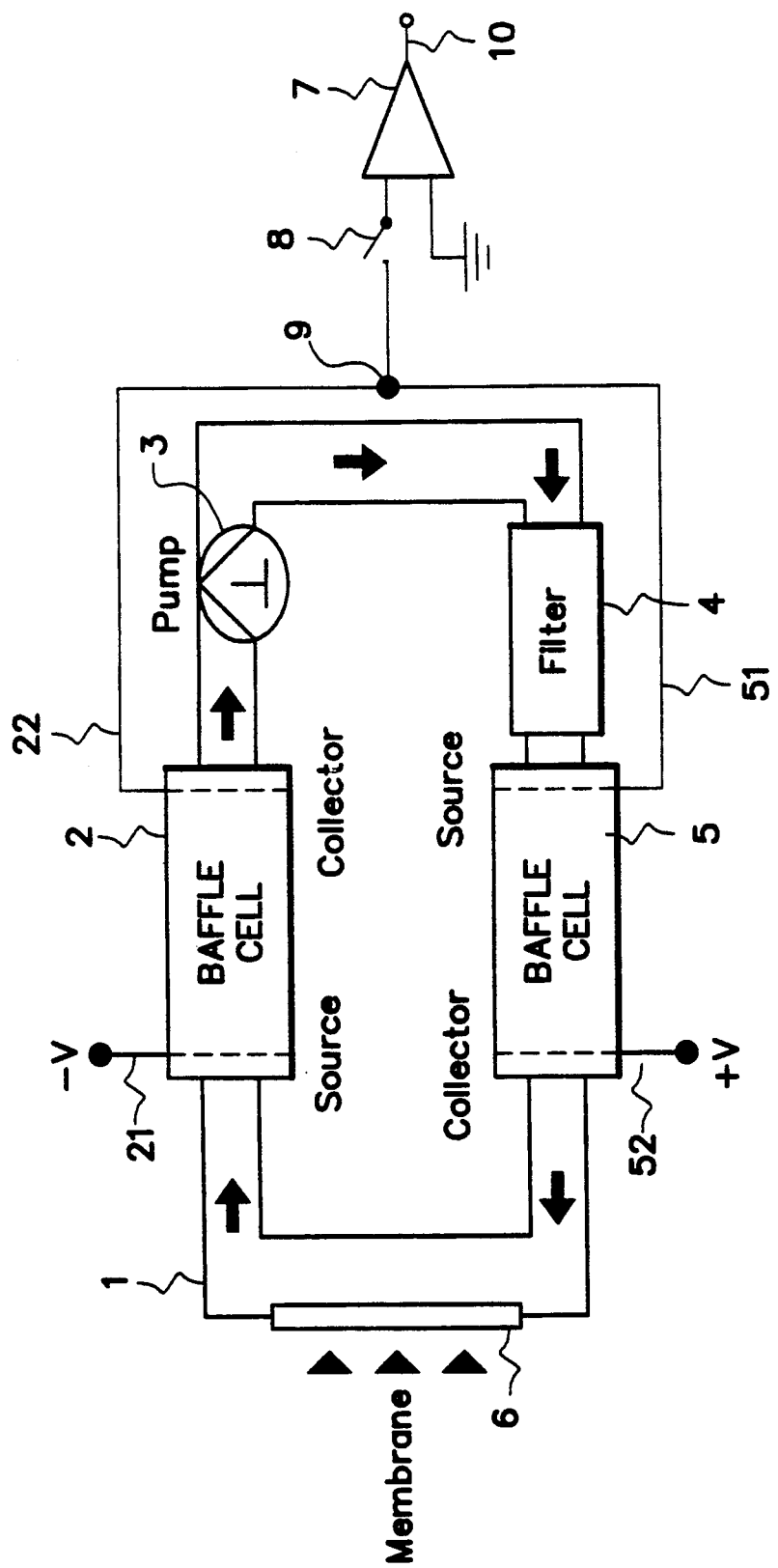
FIG. 1 shows an example for a blister agent detector comprising a closed gas loop in accordance with the invention.

FIG. 1 shows a closed loop gas channel 1 in which a first baffle cell 2, a pump 3, a filter 4 and a second baffle cell 5 are positioned one behind the other. The gas which has to be investigated is supplied into this gas channel 1 via a water vapor barrier formed by a diaphragm 6. The two baffle cells 2 and 5 may have the structure as known from U.S. Pat. No. 3,835,328. Each of them comprises a source electrode 21 and 51, respectively, and a collector electrode 22 and 52, respectively. For ionizing the gas molecules flowing through the cell and therewith for forming gas clusters enriched with molecules of the trace gases, each of the two baffle cells 2 and 5 comprises a radioactive radiation source, e.g. a foil coated with the radioactive element Americium 241. The carrier gas (air) ions recombine during their flow through the labyrinth path of the cells. However, negative clusters enriched with blister agents do not recombine. These clusters rather move through cell 2 and generate a current at its collector 22. Filter 4 removes all trace gas portions from the gas stream and for this purpose may be an active charcoal filter. Simultaneously this filter comprises a dryer in order to remove remaining water vapor molecules from the gas loop. Therefore, an ionized trace gas-free carrier gas flows through cell 5. The electrical signal generated at collector electrode 52, therefore, only depends on the flow of carrier gas ions. The formation of a differential signal derived from the output signals of both cells 2 and 5 is achieved by connecting together at junction 9 the collector electrode 22 of the first baffle cell 2 and the source electrode 51 of the second baffle cell 5. Junction 9 is connected to the input of preamplifier 7. A switch 8 periodically interrupts the differential current and during the current pauses the differential amplifier works with open or grounded input and therewith by means of a control circuit can be automatically adjusted and balanced. All noise or interference caused by temperature changes of the gas or of the measuring apparatus or caused by changes of the supply voltage at the two baffle cells or by changes of the speed of the pump will effect the output signals of both baffle cells in the same sense and amount and therefore are compensated by the difference-forming circuit. Both baffle cells 2 and 5 are chosen such that their characteristic values correspond to each other. The measuring apparatus may be balanced or adjusted by first feeding the apparatus with a carrier gas which does not comprise any trace gases, and at the output 10 of preamplifier 7 the subsequent measuring circuit is balanced such that it in this case shows a zero output signal (no trace gases). The source electrode 21 of the first baffle cell 2 and the collector electrode 52 of the second baffle cell 5 are connected to voltages ($-20$ V and $+29$ V, respectively) of identical amplitude but opposite polarity.

Figure 2:
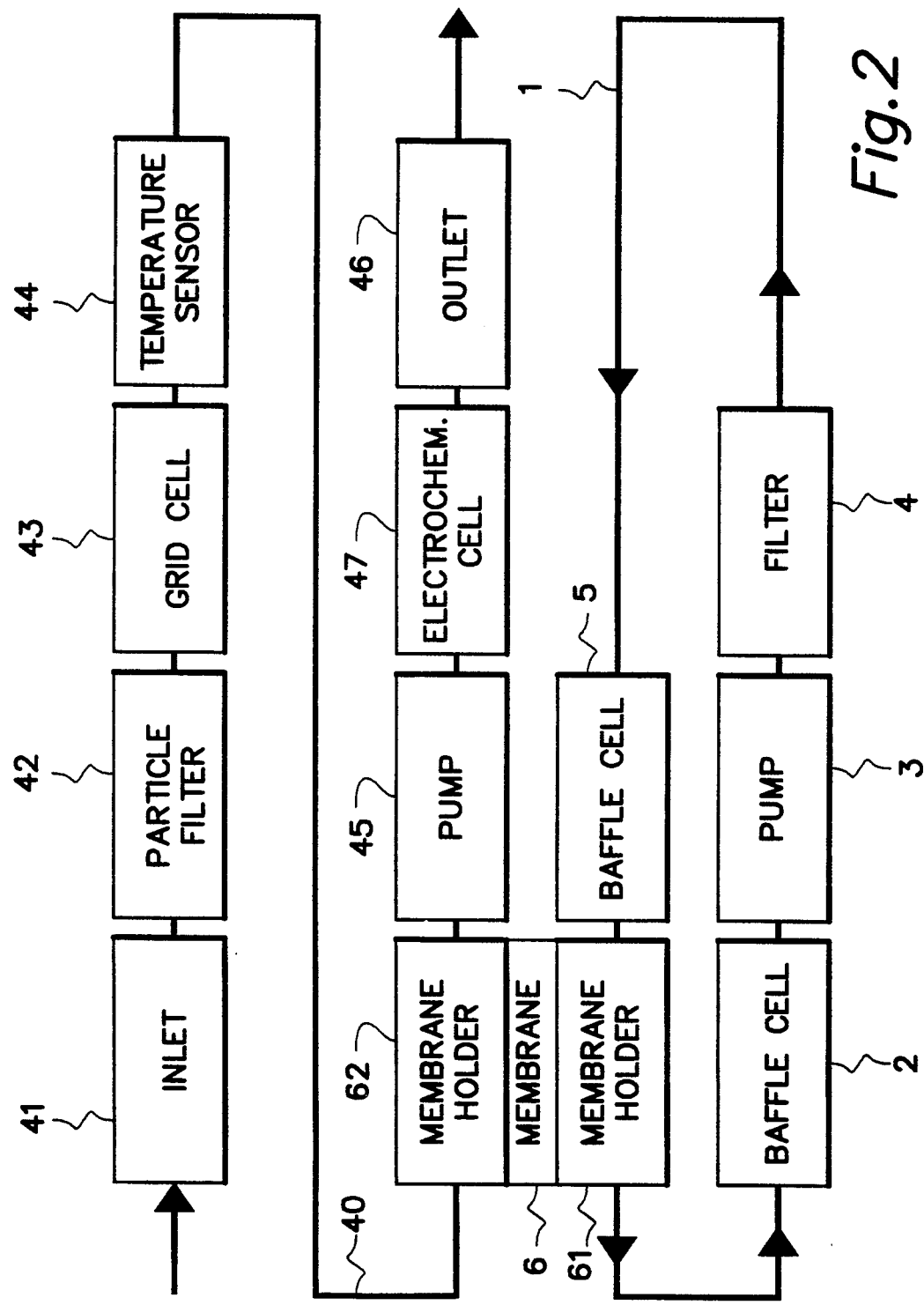
FIG. 2 shows the combination of such detector with two further detectors into a single compact universal war gas detector unit, whereat a second detector comprises a dynamic grid cell for nerve agent detection and the third detector is an electrochemical cell for the detection of shocking agents.

The combined war gas detector shown in FIG. 2 includes in its lower portion the blister agent detector as described above with reference to FIG. 1 which is coupled to the flow path 40 of a further detector via diaphragm 6. This diaphragm or membrane 6 is provided between a membrane holder 61 of the blister agent detector and a membrane holder 62 of the second flow path 40. The second detector comprises between its gas inlet 41 and the aforementioned membrane holder 62 a second detector module comprising a particle filter 42, a dynamic grid cell 43 and a temperature sensor 44. An example of such a second detector responsive to shocking agents is known from U.S. Pat. No. 4,775,795. The gas flow through the dynamic grid cell 43 is accomplished by a ventilator or a pump 45. An electrochemical cell 47 is provided between said pump and the gas outlet 46. This electrochemical cell 47 may be used for the detection of shocking agents. The structure of this electrochemical cell 47 is not part of this invention. The block diagram according to FIG. 2 further shows that here three filter modules are combined to a compact war gas detector with these three modules responding to all presently known war gases. None of the baffle cells 43, 2 and 5 requires a high voltage supply and for detecting the various war gases no chemicals must be supplied, monitored and disposed. The principle of the present invention, namely using two baffle cells connected via a filter into a closed gas loop and forming the difference of the output signals, cannot only be used for detecting mustard gas or other war agents, but may also be used for detecting other trace gases.

We claim:

1. Apparatus for detecting trace gases in a gas mixture, wherein a stream of the gas mixture driven by a first gas flow generating means flows through first and second baffle cells and through a filter positioned between them, with said filter removing the trace gas to be detected, said apparatus comprising an arrangement in which:

a) each baffle cell includes
      a source electrode forming
      a radiation source for ionizing molecules of the gas mixture,
      a recombination zone downstream of said source electrode, and
      a collector electrode downstream of said recombination zone;

b) the first and second baffle cells, together with the filter and the first gas flow generator, constitute a closed gas loop;

c) the source electrode of the first baffle cell and the collector electrode of the second baffle cell are connected to supply voltages having identical amplitudes, but opposite polarity; and d) the collector electrode of the first baffle cell and the source electrode of the second baffle cell are connected together and are connected to the input of a preamplifier for producing a signal corresponding to the concentration of a first trace gas to be detected.

2. The apparatus according to claim 1 wherein the filter comprises a gas drying means for stabilizing the dew point of the gas.

3. The apparatus according to claim 1 or 2, including a water vapor barrier at an inlet of the closed gas loop upstream from the first baffle cell for preventing water vapor from entering said closed gas loop.

4. The apparatus according to claim 3 wherein said water vapor barrier is between the closed gas loop and a first separate measuring system which is sensitive to a second trace gas different from the first trace gas.

5. The apparatus according to claim 4 wherein said first separate gas measuring system sensitive to a second trace gas comprises a grid cell for ion mobility spectroscopy, and said water vapor barrier is exposed to the gas stream downstream of said grid cell.

6. The apparatus according to claim 5 wherein a second gas flow generating means is provided within the gas flow path through said first separate gas measuring system.

7. The apparatus according to claim 6 wherein a second separate gas measuring system is provided downstream of the second gas flow generating means, said second separate gas measuring system including an electrochemical measuring cell responsive to a third trace gas different from the first and second trace gases.

* * * * *